US 7,459,579 B2
Dec. 2, 2008

(12) United States Patent
Kudo et al.

(54) METHOD OF SEPARATING OPTICALLY ACTIVE DIHYDROXY-HEPTENOIC ACID ESTERS

(75) Inventors: Keiko Kudo, Tsukuba (JP); Kozo Tachibana, Tsukuba (JP); Koichi Murazumi, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 264 days.

(21) Appl. No.: 11/254,856

(22) Filed: Oct. 21, 2005

(65) Prior Publication Data

US 2006/0079708 A1     Apr. 13, 2006

Related U.S. Application Data

(63) Continuation of application No. PCT/JP2004/005924, filed on Apr. 23, 2004.

(30) Foreign Application Priority Data

Apr. 24, 2003 (JP) .............................. 2003-119819

(51) Int. Cl.
*C07C 69/76* (2006.01)
*C08B 15/06* (2006.01)
*C08B 37/00* (2006.01)

(52) U.S. Cl. .............................. 560/60; 536/30; 536/53
(58) Field of Classification Search ............... 560/61, 560/60; 536/53, 30
See application file for complete search history.
eb;normal

(56) References Cited

U.S. PATENT DOCUMENTS

| 5,939,552 | A | 8/1999 | Ikeda et al. |
| 6,217,774 | B1 | 4/2001 | Nagamatsu et al. |
| 6,946,557 | B2 * | 9/2005 | Onishi et al. ................. 546/173 |
| 2005/0075502 | A1 | 4/2005 | Onishi et al. |

FOREIGN PATENT DOCUMENTS

| EP | 1 331 214 A1 | 7/2003 |
| EP | 1 354 865 A1 | 10/2003 |
| JP | 1-290635 A | 11/1989 |
| WO | WO-97/23778 A1 | 7/1997 |
| WO | WO-02/30853 A1 | 4/2002 |

* cited by examiner

*Primary Examiner*—Taylor Victor Oh
(74) *Attorney, Agent, or Firm*—Birch, Stewart, Kolasch & Birch, LLP.

(57) ABSTRACT

An optically active dihydroxyheptenoic acid ester having an aromatic group is separated from a solution containing a mixture of optical isomers of digydroxyheptenoic acid ester by liquid chromatography with a packing material constituted of a carrier and a polysaccharide derivative carried on the carrier. The polysaccharide derivative is a polysaccharide in which the hydrogen atoms constituting the hydroxyl and amino groups are partially or all replaced by one or more kinds of groups selected from among carbamoyl groups monosubstituted with aromatic groups having specific alkyl groups and benzoyl groups having specific alkyl groups. According to the invention, optically active dihydroxyheptenoic acid esters can be separated more distinctly.

12 Claims, 9 Drawing Sheets

METHOD OF SEPARATING OPTICALLY ACTIVE DIHYDROXY-HEPTENOIC ACID ESTERS

This application is a continuation of international application PCT/JP2004/005924, which was filed Apr. 23, 2004 and which designated the United States. The entire disclosure of PCT/JP2004/005924 is hereby expressly incorporated by reference. Applicants claim the benefit under 35 U.S.C. §120 of the filing date of PCT/JP2004/005924. Applicants also claim the benefit, under 35 U.S.C. §119, of the filing date of JP 2003-119819, filed Apr. 24, 2003. The entire disclosure of JP 2003-119819 is hereby expressly incorporated by reference.

TECHNICAL FILED

The present invention relates to a method of separating optically active dihydroxyheptenoic acid esters, and more particularly, to a method of separating optically active dihydroxyheptenoic acid esters useful for prevention and therapy of hyperlipemia, arteriosclerosis, and the like.

BACKGROUND ART

Optical isomers, which have the same structural formula, are in a relation of mirror image to each other, since atoms therein have different arrangement spatially. It is well known that medicines that contain optical isomers exhibit considerable differences in efficacy and toxicity. Accordingly, in the Medicine Production Guideline by the Ministry of Health, Labor and Welfare, Japan, it is described that "When the drug is a racemic body, it is desirable that absorption, distribution, metabolism, and excretion behaviors of each isomer are studied."

When only one of the optical isomers is used as a therapeutic drug, the dosage of the drug can be reduced to increase efficacy per unit and reduction of side effects can be attempted. Therefore, in the field of drug- and biochemistry-related industries and so on, it is becoming an extremely important subject to prepare optically active substances having high optical purity.

Specified dihydroxyheptenoic acid esters including some optical isomers are known to be very effective for the prevention and therapy of hyperlipemia, arteriosclerosis, and so on. Examples of known methods of producing such dihydroxyheptenoic acid esters include methods of producing optically active dihydroxyheptenoic acid esters industrially using packing materials for optical resolution (see, for example, pamphlets of WO95/23125 and WO02/30903).

However, the productivity of the dihydroxyheptenoic acid esters produced by using the conventional packing material for optical resolution remains to be studied and there has been a keen demand for a method for the production of optically active dihydroxyheptenoic acid esters with more excellent productivity.

The present invention provides a method of separating optically active dihydroxyheptenoic acid esters more clearly.

DISCLOSURE OF THE INVENTION

According to one aspect of the present invention, there is provided a method of separating optically active dihydroxyheptenoic acid esters from a solution comprising a mixture of optical isomers of a dihydroxyheptenoic acid ester represented by the general formula (1) below by liquid chromatography in which a packing material including a carrier and a polysaccharide derivative carried on the carrier is used, wherein a portion or all of hydrogen atoms in hydroxyl groups and amino groups in a polysaccharide are substituted with one or more of a substituent represented by the general formula (2) below and a substituent represented by the general formula (3) below.

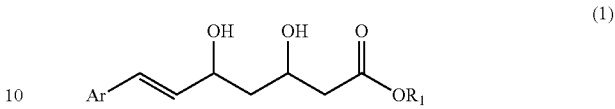

(Wherein Ar represents a carbocyclic aromatic group or a heterocyclic aromatic group that may have at least one of a substituent and a condensed ring, $R_1$ represents a linear or branched chain alkyl group having 1 to 20 carbon atoms, a phenyl group, or an aralkyl group having 7 to 18 carbon atoms.)

(Wherein $R_2$ represents a linear or branched chain alkyl group having 2 to 8 carbon atoms.)

(Wherein $R_2$ represents a linear or branched chain alkyl group having 2 to 8 carbon atoms.)

BEST MODE FOR CARRYING OUT THE INVENTION

Figure 1:
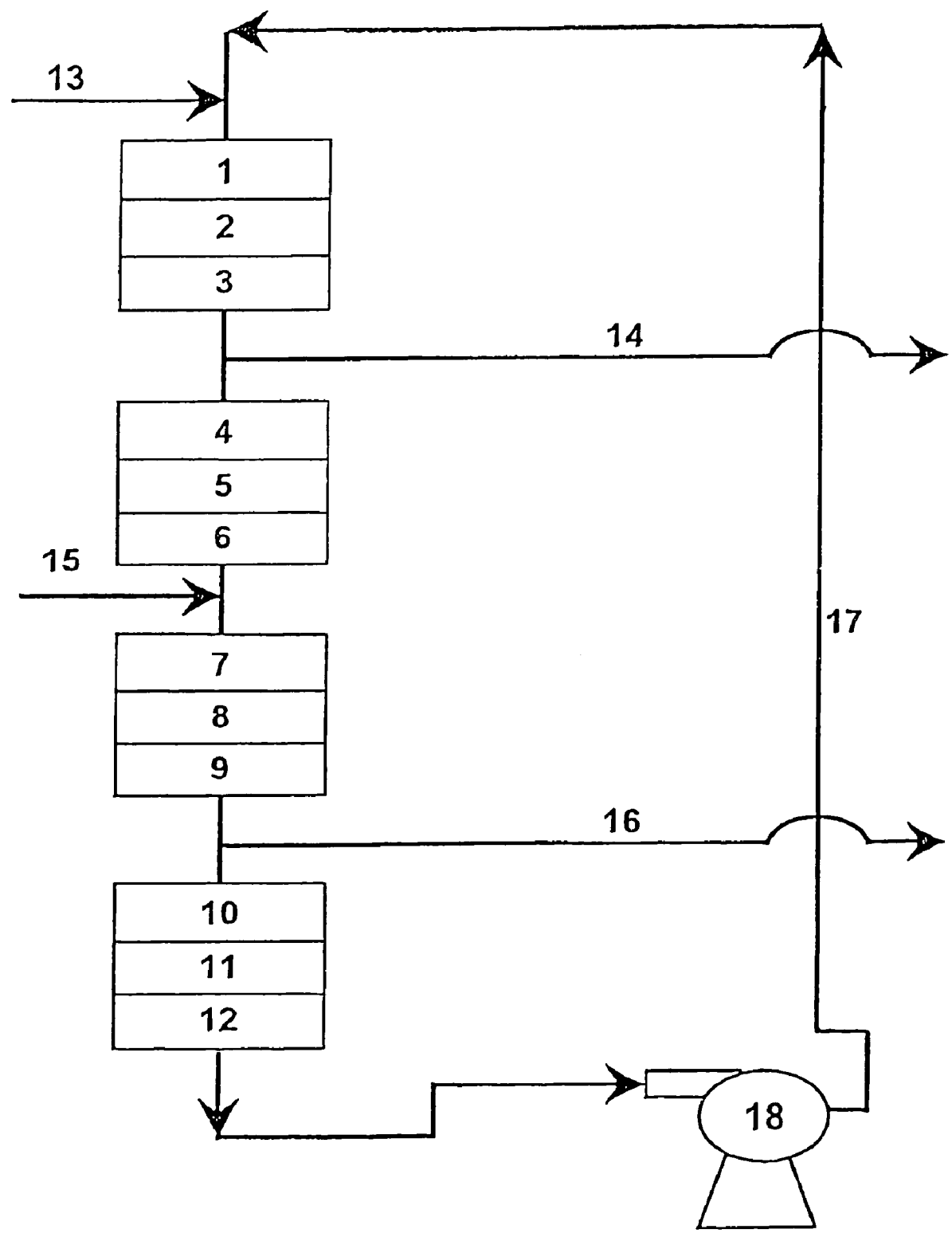
FIG. 1 is a schematic diagram showing an example of the structure of a simulated moving bed apparatus used in the present invention.

In the present invention, an optically active dihydroxyheptenoic acid ester is separated from a solution comprising a mixture of optical isomers of the dihydroxyheptenoic acid ester represented by the general formula (1) by liquid chromatography with a packing material. The packing material comprises a carrier and a polysaccharide derivative carried by the carrier.

The polysaccharide derivative is formed by substituting a portion or all of hydrogen atoms in the hydroxyl and amino groups of a polysaccharide by one or more of substituents represented by the general formula (2) and the general formula (3) above.

The polysaccharide derivative can be synthesized by a conventional method by a reaction between, for example, benzoic acid having a linear or branched chain alkyl group having 2 to 8 carbon atoms and derivatives thereof or phenyl isocyanate having the above-mentioned alkyl group and hydroxyl groups of the polysaccharide.

Examples of the benzoic acid derivative include chlorides of benzoic acid, acid anhydrides of benzoic acid, and esters of benzoic acid. The above-mentioned benzoic acid and derivatives thereof as well as the above-mentioned phenyl isocyanate can be commercially available products or synthesized by a conventional method.

The position of the alkyl group at the phenyl group of the polysaccharide derivative is not particularly limited; however, it is preferable that the alkyl group is connected to the carbon atom at the 4-position of the phenyl group in order to increase the separating effect on one optical isomer. Further, the kind of the alkyl group is not particularly limited so far as the alkyl group has 2 to 8 carbon atoms. However, the alkyl group preferably is an alkyl group having 2 to 4 carbon atoms in order to increase the separating effect on one optical isomer.

Examples of such alkyl groups include an ethyl group, an isopropyl group, an n-butyl group, an isobutyl group, and a sec-butyl group. An ethyl group, an isopropyl group, and an n-butyl group are preferable.

The polysaccharide is not particularly limited and may be any one of natural polysaccharide, natural product-denatured polysaccharide, synthetic polysaccharide, and oligosaccharide so far as it is optically active.

Specific examples of the polysaccharide include: α-1,4-glucan (amylose, starch, or glycogen); β-1,4-glucan (cellulose); α-1,6-glucan (dextran); β-1,3-glucan (curdlan, schizophyllan, or the like); α-1,3-glucan; β-1,2-glucan (Crown Gall polysaccharide); α-1,6-mannan; β-1,4-mannan; β-1,2-fructan (inulin); β-2,6-fructan (levan); β-1,4-xylan; β-1,3-xylan; β-1,4-chitosan; β-1,4-N-acetylchitosan (chitin); α-1,3-1,6-glucan (mutan); pullulan; agarose; and alginic acid.

Of those, cellulose, amylose, β-1,4-xylan, β-1,4-chitosan, chitin, β-1,4-mannan, inulin, curdlan, and so on are preferable, and cellulose and amylose are particularly preferable.

A number average polymerization degree of the polysaccharide (an average number of monosaccharide units, such as pyranose and furanose comprised in one molecule) is 5 or more, preferably 10 or more. On the other hand, although there is no upper limit in the number average polymerization degree of the polysaccharide, the number average polymerization degree is preferably 2,000 or less and particularly preferably 500 or less, from the viewpoint of easy handling.

Specific examples of the oligosaccharide include maltose, maltotetraose, maltopentaose, maltohexaose, maltoheptaose, isomaltose, erlose, palatinose, maltitol, maltotriitol, maltotetraitol, isomaltulose, α-cyclodextrin, β-cyclodextrin, and γ-cyclodextrin.

In the polysaccharide derivative used in the present invention, the degree of substitution of the hydrogen atoms by the substituent represented by the above-mentioned general formulae (2) or (3) is usually 10 to 100%, preferably 30 to 100%, particularly preferably 80% to 100%. It is preferable that the above-mentioned degree of substitution is within the above-mentioned range from the viewpoint of increasing the separating effect on one optical isomer.

The degree of substitution can be adjusted depending on, for example, the equivalent of the benzoic acid and derivative thereof or the phenyl isocyanate to the equivalent of the hydroxyl group and amino group of the polysaccharide at the time of the above-mentioned reaction. Also, the degree of substitution can be obtained by examining changes in elements such as carbon, hydrogen, and nitrogen before and after introduction of the substituent by elemental analysis.

The form of connection of the substituent to the polysaccharide in the above-mentioned polysaccharide derivative is not particularly limited. For example, the above-mentioned polysaccharide derivative may be either a polysaccharide derivative that includes a polysaccharide and a plurality of substituents of the same kind connected to the polysaccharide or a polysaccharide derivative that includes a polysaccharide and a plurality of substituents of different kinds connected to the polysaccharide.

In the case of the above-mentioned polysaccharide derivative, distribution of the substituent to the polysaccharide may be either uniform or biased. The number of the above-mentioned substituents connected to a monosaccharide unit may be either the same or different with respect to all the monosaccharide units.

The position of the above-mentioned substituent connected to the monosaccharide unit may be either a position of a specified hydroxyl or amino group in a monosaccharide unit, or not particularly regular.

The carrier used in the present invention is not particularly limited and any carrier usually used as a packing material that is packed in a column can be used. Examples of such a carrier include porous organic carriers, porous inorganic carriers, and porous organic-inorganic hybrid carriers. Porous inorganic carriers are preferable.

Suitable examples of the porous organic carriers include particles of a polymer selected from the group consisting of polystyrene, polyacrylamide, and polyacrylate, and the like.

Suitable examples of the porous inorganic carriers include silica, alumina, magnesia, glass, kaolin, titanium oxide, silicates, and hydroxyapatite.

Suitable examples of the porous organic-inorganic hybrid carriers include substances each containing an alkyl group, a phenyl group, a vinyl group, a styryl group, or the like in the molecular backbone of silica, alumina, magnesia, titanium oxide, or the like. A particularly preferable carrier is silica gel.

Preferably, silica gel has a particle size of 100 nm to 10 mm, more preferably 1 μm to 300 μm, still more preferably 1 to 75 μm. Pore on the porous surface of silica gel has an average pore size of preferably 1 nm to 100 μm and more preferably 5 nm to 500 nm. Silica gel is preferably surface treated to avoid an influence of residual silanol. However, silica gel may not be surface treated at all.

The carrying amount of the polysaccharide derivative to be carried by the carrier is usually 1 to 80 mass %, preferably 5 to 60 mass %, particularly preferably 20 to 40 mass % with respect to the packing material. When the carrying amount is less than 1 mass %, optical resolution may sometimes fail to be performed effectively while a carrying amount of more than 60 mass % is not preferable since a decrease in separation efficiency occurs owing to a decrease in the number of stages. Note that the carrying amount means a ratio between the mass of the packing material and the mass of the polysaccharide derivative in the packing material.

The packing material used in the present invention can be obtained by having the polysaccharide derivative carried by the carrier. Having the polysaccharide derivative carried by the carrier can be performed by a method usually used for preparing a packing material for chromatography. Examples of such a method include a method in which the polysaccharide derivative is chemically connected directly to the carrier, and a method in which a solution containing a polysaccharide derivative is applied to a carrier and then the solvent is distilled off.

The solvent used for dissolving the polysaccharide derivative in the above-mentioned method may be any conventionally used organic solvent so far as it can dissolve the polysaccharide derivative.

Further, further chemical bonds may be formed by chemical bonds between a carrier and the polysaccharide derivative on the carrier, chemical bonds between the polysaccharide derivatives on the carrier, chemical bonds utilizing a third component that intervenes between the carrier and the polysaccharide derivative, reactions by irradiation to the polysaccharide derivative on the carrier with light, radioactive ray such as γ-ray, or electromagnetic wave such as microwave, and a reaction based on the generation of a radical due to a radical initiator, or the like, to immobilize the polysaccharide derivative onto the carrier more firmly.

The optically active dihydroxyheptenoic acid ester separated by the packing material is represented by the general formula (1) above.

In the general formula (1) above, $R_1$ is not particularly limited so far as it is a linear or branched chain alkyl group having 1 to 20 carbon atoms, a phenyl group, or an aralkyl group. The alkyl group has preferably 1 to 20 carbon atoms, more preferably 1 to 8 carbon atoms, and still more preferably 2 to 5 carbon atoms.

The aromatic group in the aralkyl group preferably has 6 to 14 carbon atoms and may have either one of or both of a hetero atom and a condensed ring. The alkylene group in the aralkyl group preferably has 1 to 4 carbon atoms, which may be a linear or branched chain.

Ar in the general formula (1) is an aromatic group that may have a hetero atom and includes a condensed polycyclic aromatic group. Examples of such Ar include a phenyl group, a naphthyl group, an indenyl group, a pyridyl group, a quinolyl group, and an indolyl group.

The substituents that Ar may have are not particularly limited so far as the effects of the present invention are not damaged. Examples of the substituents include: substituents composed only of a hetero atom such as a nitro group; substituents each containing a hetero atom such as an amino group, a hydroxyl group, and an alkoxy group; halogen groups such as fluorine and chlorine; and hydrocarbon groups such as an alkyl group and a phenyl group each of which may have these substituents.

Specific examples of the dihydroxy-heptenoic acid esters include methyl [R*,S*-(E)]-(±)-[3-(4-fluorophenyl)-1-(1-methylethyl)-1H-indol-2-yl]-3,5-dihydroxy-6-heptenoate represented by the following structural formula (4) and ethyl [R*,S*-(E)]-(±)-[3-(4-fluorophenyl)-1-(1-methylethyl)-1H-indol-2-yl]-3,5-dihydroxy-6-heptenoate represented by the following structural formula (5).

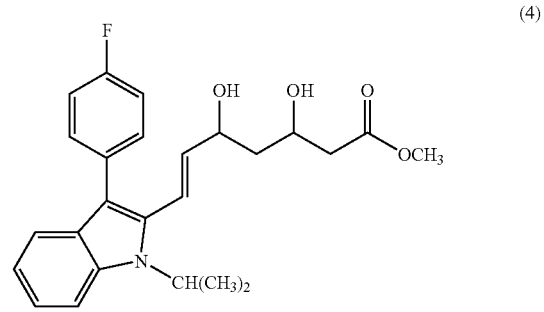

(4)

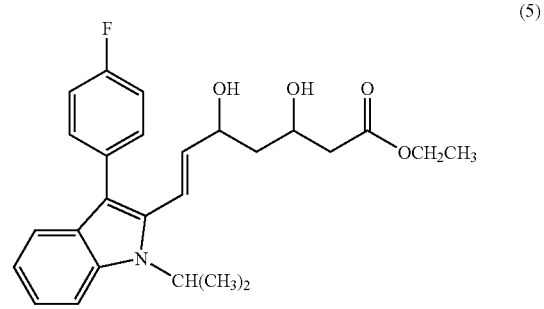

(5)

The mixture of optical isomers of the dihydroxyheptenoic acid ester is not particularly limited so far as at least one of the optical isomers in the mixture contains an optical isomer that is separated by the above-mentioned polysaccharide derivative, but the mixture is preferably one of 3S5R form and 3R5S form.

The mixture may be a mixture of mirror isomers such as a mixture of 3S5R form and 3R5S form, a mixture containing a diastereomer such as a mixture of 3S5R form or 3R5S form and 3S5S form or 3R5R form, or a mixture of these mixtures.

In the present invention, the above-mentioned optical isomers can be separated by column chromatography in which the optical isomers are moved in the packing material as a fixed phase by a supercritical fluid or general solvent or mixed solvent as a moving phase with supplying a mixed solution containing at least optical isomers of the dihydroxyheptenoic acid ester represented by the general formula (1) to the fixing phase. In the present invention, it is preferably that liquid chromatography is applied from the viewpoint of separation of the optical isomers.

A solvent such as a mixed solvent that can dissolve the above-mentioned mixture can be used as the mixed solution. The kind and composition of such a solvent are determined depending on the kind and concentration of the solute. A solvent that is used in ordinary liquid chromatography can be used as the solvent.

The solvent used in the mixed solution is preferably a moving phase in liquid chromatography or a method similar thereto, that is, an eluent from the viewpoint of making reuse of eluent easy. The mixed solution may contain other components so far as the components can be separated from the optical isomers by the column chromatography.

In the present invention, the optically active dihydroxyheptenoic acid ester can be obtained by: collecting a solution of one of the optical isomers that is separated by ordinary column chromatography; and evaporating the solvent from this solution.

In such a production method for the optically active dihydroxyheptenoic acid ester, it is preferable that separation of the optically active dihydroxyheptenoic acid ester be performed by batch-type chromatography in which at least one of the supply of the sample and the discharge of the liquid is performed discontinuously, or simulated moving bed chromatography in which the supply of the sample and the discharge of the liquid are performed continuously from the viewpoint of increasing the productivity of fractionation of the optically active dihydroxyheptenoic acid ester.

In particular, in the case of producing the optically active dihydroxyheptenoic acid ester, it is more preferable that simulated moving bed chromatography is used. In the simulated moving bed chromatography, a solvent that is usually used in this method can be used as a moving phase.

The simulated moving bed chromatography comprises the steps of: supplying an eluent in an endless conduit formed by connecting in series a plurality of columns each having packed therein the above-mentioned packing material; discharging a portion of a liquid that flows in the conduit at a position downstream of the supplying position where the eluent is supplied in the direction of flow of the eluent in the conduit (hereinafter, also referred to as a "first discharging step"); supplying the mixed solution at a position downstream of the position of discharging the liquid in the direction of flow of the eluent in the conduit (hereinafter, also referred to as a "first discharging position"); discharging a portion of a liquid that flows in the conduit at a position between the supplying position of the mixed solution and the supplying position of the eluent (hereinafter, also referred to as a "second discharging step", and the position of discharging the liquid in this step is also referred as a "second discharging position"); moving the supplying position of the eluent, the first discharging position, the supplying position of the mixed solution, and the second discharging position toward a downstream direction of flow of the liquid while maintaining relative positional relationship of these positions so that the mixed solution can be supplied to the position of a mixed component in the mixed solution in the conduit; and extracting the component contained in the liquid to be discharged from the conduit.

In the simulated moving bed chromatography, a component that is easy to adsorb on the packing material (hereinafter, also referred to as an "extract component") and a component that is hard to adsorb on the packing material (hereinafter, also referred to as a "raffinate component") in the mixed solution are adsorbed by the packing material in the conduit.

The extract component has a moving speed in the conduit smaller than the moving speed of the raffinate component and the moving speed of the supplying position of the mixed solution and hence the extract component distributes on the upstream side of the supplying position of the mixed solution.

On the other hand, the raffinate component has a moving speed in the conduit larger than the moving speed of the extract component and the moving speed of the supplying position of the mixed solution and hence the raffinate component distributes on the downstream side of the supplying position of the mixed solution.

The concentration of each component supplied from the supplying position of the mixed solution increases with time until equilibrium is reached and the concentration distribution of the extract component distributes on the upstream side of the supplying position of the mixed solution with a neighborhood of the supplying position of the mixed solution being top. On the other hand, the concentration distribution of the raffinate component distributes on the downstream side of the supplying position of the mixed solution with a neighborhood of the supplying position of the mixed solution being top.

When both the ends of the concentration distribution of each component that extends with time reaches each discharging position, solutions containing respective components are discharged from the conduit. The concentration and distribution of each component are adjusted depending on various conditions such as the size of the column, kind of the packing material, kind and supply speed of the liquid to be supplied to the conduit, speed of each liquid discharged from the conduit, and relative positional relationship between the supplying positions and discharging positions and moving speed of the positions (switching speed).

Note that the above-mentioned mixed component is a component in which the extract component and the raffinate component in the mixed solution are mixed. The position of the mixed component is not particularly limited so far as it is a potion in the conduit where the extract component and the raffinate component coexist. However, a position where the extract component and the raffinate component coexist in equal amounts is preferable.

The relative positional relationship of the supplying position of the eluent, the first discharging position, the supplying position of the mixed solution, and the second discharging position may be either a substantially equal distance positional relationship or a different distance positional relationship. The time at which those positions are moved can be determined by analysis of components in the liquid that flows in the conduit or computer simulation in which various conditions such as the kind of the packing material and the flow rate of the liquid in the conduit are set.

The simulated moving bed liquid chromatography is performed using a conventional simulated moving bed (SMB) apparatus disclosed in, for example, WO95/23125 pamphlet or JP-A-09-206502.

Hereinafter, the method of the present invention is explained with reference to the drawings.

Figure 2:
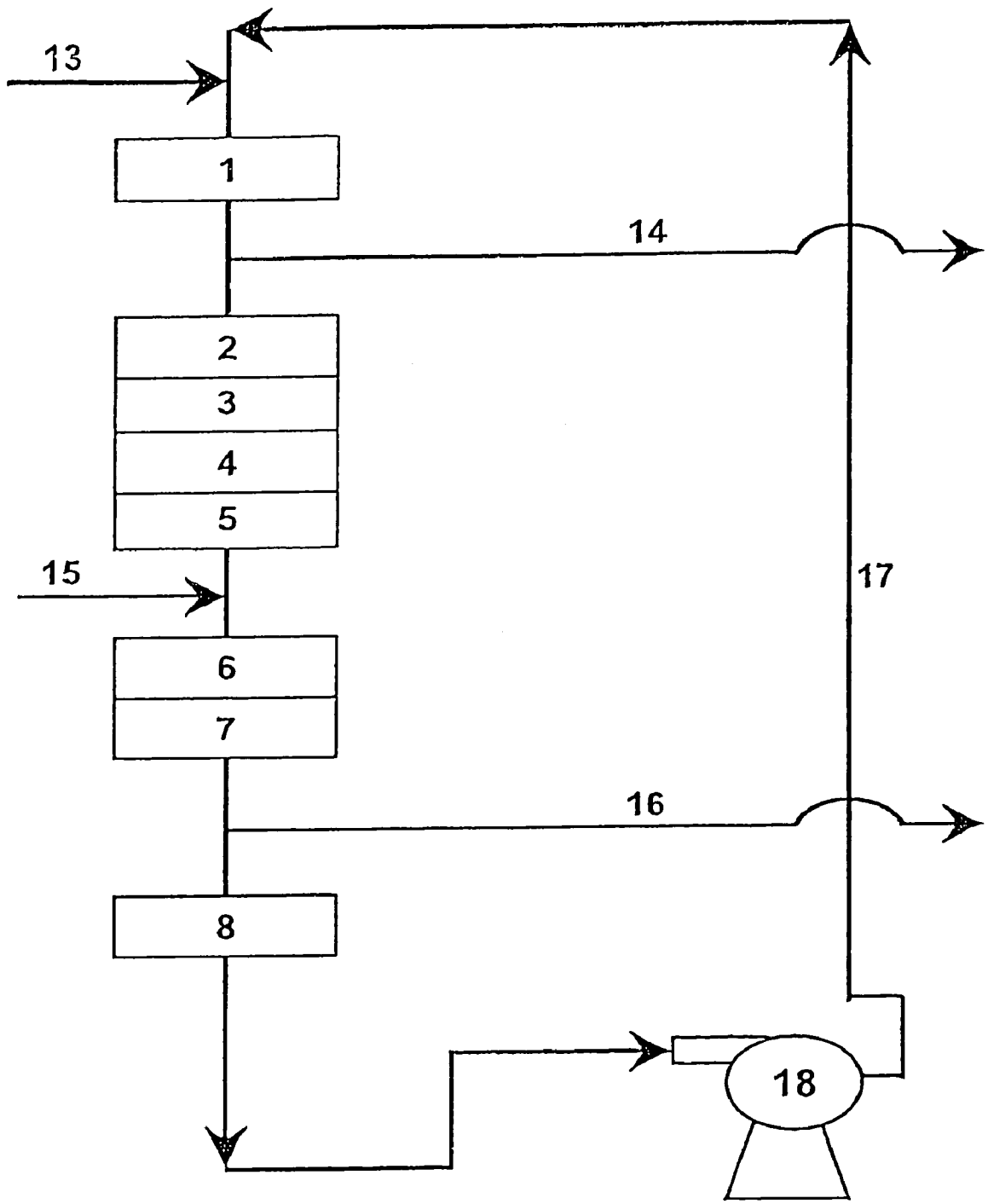
FIG. 2 is a schematic diagram showing another example of the structure of the simulated moving bed apparatus used in the present invention.

FIG. 1 is a schematic diagram showing an example of a simulated moving bed apparatus used in the present invention. FIG. 2 is a schematic diagram showing another example of a simulated moving bed used in the present invention. In FIG. 1, the conduit is formed by connecting twelve columns in series. In FIG. 2, the conduit is formed by connecting eight columns in series.

In each apparatus, though not shown, a conduit for supplying an eluent, a conduit for supplying a mixed solution, and conduits for discharging a liquid are connected to all conduits connecting the columns respectively. Supply of the liquid and discharge of the liquid to and from the conduits are controlled by automatic valves.

The number and size of the columns are determined based on factors such as the kind, composition, and flow rate of the mixed solution as well as pressure drop and size of apparatus and are not particularly limited.

In the simulated moving bed chromatography involving use of the above-mentioned apparatus, the following adsorption operation, concentration operation, desorption operation, and eluent recovering operation as basic operations are continuously and recurringly performed.

(1) Adsorption Operation

The mixed components in the mixed solution contact the packing material and adsorption and desorption are repeated by the flow of the eluent that is supplied. Since the degree of adsorption of the extract component by the packing material is greater than the degree of adsorption of the raffinate component by the packing material, the moving speed of the extract component in the column is lower. Since the degree of adsorption of the raffinate component by the packing material is smaller than the degree of adsorption of the extract component by the packing material, the moving speed of the raffinate component in the column is higher, so that the concentration distribution of the raffinate component precedes the concentration distribution of the extract component in the conduit.

(2) Concentration Operation

When an eluent containing the extract component is supplied to a packing bed on which mainly the extract component is adsorbed, the raffinate component remaining on the packing material is expelled and the extract component is concentrated.

(3) Desorption Operation

When the eluent in an amount larger than that at the time of concentrating the extract component is supplied to the packing bed, the extract component adsorbed to the packing material until then is desorbed from the packing material. As a result, in that the moving speed of the extract component in the column becomes higher than that at the time of concentration operation.

(4) Eluent Recovering Operation

When the amount of the eluent supplied to the packing material that adsorbs thereon the raffinate component becomes smaller than that at the time of adsorption of the raffinate component, the movement of the raffinate component that moves in the conduit is suppressed. The packing material on the downstream side of the point where the supply amount of the eluent decreases adsorbs component in the eluent and the eluent containing no such component is supplied to the conduit on the downstream side of the above-mentioned point.

In FIG. 1, reference numerals 1 to 12 designate chambers in each of which the packing material is contained (adsorption chamber, column), which are connected in series. Reference numeral 13 designates an eluent supply line; 14, an extract extracting line; 15, an optical isomer-containing liquid supply line; 16, a raffinate extracting line; 17, a recycle line; and 18, a pump.

In the arrangement of the adsorption chambers 1 to 12 and the respective lines 13 to 16 shown in FIG. 1, the desorption operation is performed in the adsorption chambers 1 to 3, the concentration operation is performed in the adsorption chambers 4 to 6, the adsorption operation is performed in the adsorption chambers 7 to 9, and the eluent recovering operation is performed in the adsorption chambers 10 to 12, respectively. In such a simulated moving bed, respective liquid supply lines and extracting lines are moved by one adsorption chamber in the direction of flow of the liquid in the conduit by operation of valves at predetermined time intervals.

Therefore, in the next arrangement of the next adsorption chambers, the desorption operation is performed in the adsorption chambers 2 to 4, the concentration operation is performed in the adsorption chambers 5 to 7, the adsorption operation is performed in the adsorption chambers 8 to 10, and the eluent recovering operation is performed in the adsorption chambers 11 to 1, respectively. By sequentially performing those operations, the separation treatment of a mixture of optical isomers is achieved continuously and efficiently.

In FIG. 1, the extract solution extracted from the extract extracting line 14 is supplied to a first falling film evaporator, a second falling film evaporator, and a wiped film evaporator sequentially and concentrated thereby. The vapor from the evaporator can be reused as an eluent, for example, by receiving it in a recovering tank and adjusting the composition by means of an evaporating apparatus.

The concentrate that is concentrated by the evaporators is sent to a reservoir and subjected to operations such as recrystallization and distillation to obtain the objective optically active substance from the concentrate.

Note that the raffinate solution extracted from the raffinate extracting line 16 may be mixed with a mixed solution through a racemization tank and subjected again to separation by the above-mentioned chromatography.

Although the simulated moving bed apparatus shown in FIG. 1 is an apparatus intended to produce the extract component as a target, an apparatus that is adapted to produce the raffinate component as a target can be constructed by connecting the equipment such as the evaporators or the evaporating apparatus to the downstream side of the raffinate extracting line 16.

An apparatus for producing both the extract component and the raffinate component as targets can be constructed by providing the above-mentioned equipment such as the evaporators or the evaporating apparatus for each of the extract extracting line 14 and the raffinate extracting line 16 in the simulated moving bed apparatus shown in FIG. 1.

In the arrangement of the adsorption chambers 1 to 8 and the respective lines 13 to 16 shown in FIG. 2, the eluent recovering operation is performed in the adsorption chamber 1, the adsorption operation is performed in the adsorption chambers 2 to 5, the concentration operation is performed in the adsorption chambers 6 and 7, and the desorption operation is performed in the adsorption chamber 8. In such a simulated moving bed, respective supply lines and extracting lines are moved by one adsorption chamber in the direction of flow of the liquid in the conduit by operation of valves at predetermined time intervals.

Therefore, in the next arrangement of the adsorption chambers, the desorption operation is performed in the adsorption chamber 2, the concentration operation is performed in the adsorption chambers 3 to 6, the adsorption operation is performed in the adsorption chambers 7 and 8, and the eluent recovering operation is performed in the adsorption chamber 1. By sequentially performing those operations, the separation treatment of a mixture of optical isomers is achieved continuously and efficiently.

By the method of the present invention, at least one of the optical isomers of the dihydroxyheptenoic acid ester can be separated efficiently and optically active dihydroxyheptenoic esters can be obtained with high productivity of fractionation. The obtained optically active dihydroxyheptenoic acid esters can be used as active ingredients of drugs.

The above-mentioned dihydroxyheptenoic acid esters can be used as intermediates for producing any of optical isomers of a compound represented by the following general formula (6) and any of optical isomers of a mevalonolactone-based compound represented by the following general formula (7) useful for drugs and the like by known reactions such as an oxidation reaction and a dehydration-condensation reaction.

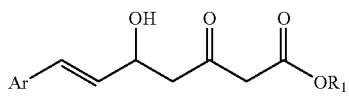
(6)

(wherein Ar represents a carbocyclic aromatic group or a heterocyclic aromatic group that may have either one of a substituent and a condensed ring, and $R_1$ represents a linear or branched chain alkyl group having 1 to 20 carbon atoms, a phenyl group, or an aralkyl group having 7 to 18 carbon atoms.)

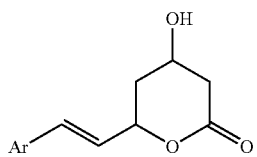
(7)

(wherein Ar represents a carbocyclic aromatic group or a heterocyclic aromatic group that may have either one of a substituent and a condensed ring.)

EXAMPLE

Hereinafter, the present invention is explained in detail by examples. However, the present invention is not limited to the examples.

Synthesis Example 1

Production of methyl [R*,S*-(E)]-(±)-[3-(4-fluorophenyl)-1-(1-methylethyl)-1H-indol-2-yl]-3,5-dihydroxy-6-heptenoate (1) Extraction of sodium [R*,S*-(E)]-(±)-[3-(4-fluorophenyl)-1-(1-methylethyl)-1H-indol-2-yl]-3,5-dihydroxy-6-heptenoate Sodium [R*,S*-(E)]-(±)-[3-(4-fluorophenyl)-1-(1-methylethyl)-1H-indol-2-yl]-3,5-dihydroxy-6-heptenoate represented by the following structural formula (8) was extracted from a drug Lescol (registered trade mark of NOVARTIS) manufactured by NOVARTIS by heating under reflux of chloroform. The obtained sample was measured by $^1$H-NMR, COSY, $^{13}$C-NMR, HMQC, and IR, and the extract was identified by the obtained spectra. Peaks detected by $^1$H-NMR, $^{13}$C-NMR, and IR are shown in the following.

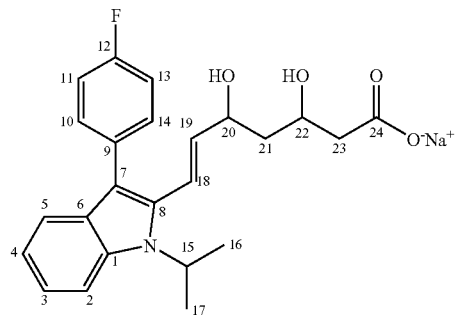
(8)

$^1$H-NMR (DMSO-$d_6$): δ 1.30 (m, 1H, H21), 1.53 (m, 1H, H21), 1.55 (d, J=6.9 Hz, 6H, H16, H17), 1.89 (m, 1H, H23), 2.09 (m, 1H, H23), 3.73 (m, 1H, H22), 4.23 (m, 1H, H20), 4.88 (m, 1H, H15), 5.70 (dd, $J_1$=16.0 Hz, $J_2$=5.4 Hz, 1H, H19), 6.59 (d, J=15.7 Hz, 1H, H18), 7.0-7.6 (m, 8H, H2-H5, H10, H11, H13, H14)

$^{13}$C-NMR (DMSO-$d_6$): δ 21.5 (C16, C17), 43.7 (C23), 44.5 (C24), 47.2 (C10), 65.9 (C22), 69.0 (C20), 112.1 (C2), 115.4 (C11, C13), 116.9 (C18), 118.7 (C5), 119.6 (C4), 121.6 (C3), 141.8 (C19), 159.8 (C12), 161.7 (C8) (it should be noted that 113.0, 127.7, 134.3, and 134.8 correspond to C1, C6, C7, and C9 of quaternary carbon)

IR (KBr disk): 3,000 to 2,850 (w, C—H stretching), 1,580 (s, C=O stretching), 1,500 (m, substituted aromatics), 1,345 (m), 1,220 (s), 1,155 (m), 1,105 (w), 970 (w), 835 (m, p substituted aromatics), 740 (m, substituted aromatics)

(2) Methyl esterification of sodium [R*,S*-(E)]-(±)-[3-(4-fluorophenyl)-1-(1-methylethyl)-1H-indol-2-yl]-3,5-dihydroxy-6-heptenoate The sodium [R*,S*-(E)]-(±)-[3-(4-fluorophenyl)-1-(1-methylethyl)-1H-indol-2-yl]-3,5-dihydroxy-6-heptenoate obtained in the above item (1) was reacted with excessive methyl iodide in a solution of dimethylformamide solution using lithium carbonate as a catalyst and the obtained oily component was extracted with diethyl ether. The obtained sample was measured by $^1$H-NMR, MS, and IR, and the extract was identified by the obtained spectra. Peaks detected by $^1$H-NMR and IR are shown in the following.

$^1$H-NMR (DMSO-$d_6$): δ 1.41 (m, 1H), 1.59 (d, J=7.0 Hz, 6H), 2.30 (dd, $J_1$=14.8 Hz, $J_2$=8.6 Hz, 1H), 2.44 (dd, $J_1$=14.8 Hz, $J_2$=4.3 Hz, 1H), 3.58 (s, 3H), 3.87 (m, 1H) 4.24 (m, 1H), 4.50 (m, 1H), 4.90 (m, 1H), 5.70 (dd, $J_1$=16.1 Hz, $J_2$=5.8 Hz, 1H), 6.69 (d, J=15.7 Hz, 1H), 7.0-7.6 (m, 8H)

IR (KBr disk): 3,050 to 2,850 (w, C—H stretching), 1,720 (s, C=O stretching), 1,545 (m), 1,500 (m, substituted aromatics), 1,345 (m), 1,220 (s), 1,155 (m), 1,100 (w), 970 (w), 835 (m, p substituted aromatics), 740 (m, substituted aromatics)

Synthesis Example 2

Production of ethyl [R*,S*-(E)]-(±)-[3-(4-fluorophenyl)-1-(1-methylethyl)-1H-indol-2-yl]-3,5-dihydroxy-6-heptenoate (1) Extraction of sodium [R*,S*-(E)]-(±)-[3-(4-fluorophenyl)-1-(1-methylethyl)-1H-indol-2-yl]-3,5-dihydroxy-6-heptenoate This compound was obtained by the same technique as in Synthesis Example 1 (1)

(2) Ethyl esterification of sodium [R*,S*-(E)]-(±)-[3-(4-fluorophenyl)-1-(1-methylethyl)-1H-indol-2-yl]-3,5-dihydroxy-6-heptenoate This compound was obtained by the same technique as in Synthesis Example 1 (2) except that methyl iodide was replaced by ethyl iodide. The obtained sample was measured by $^1$H-NMR, MS, and IR, and the extract was identified by the obtained spectra. Peaks detected by $^1$H-NMR and IR are shown in the following.

$^1$H-NMR (DMSO-d$_6$): δ 1.16 (t, J$_1$=7.1 Hz, J$_2$=7.1 Hz, 3H), 1.58 (d, J=7.0 Hz, 6H), 2.29 (dd, J$_1$=14.8 Hz, J$_2$=8.5 Hz, 1H), 2.42 (dd, J$_1$=14.8 Hz, J$_2$=4.5 Hz, 1H), 3.4 (m, 1H), 3.87 (m, 1H), 4.02 (q, J=7.0 Hz, 2H), 4.23 (m, 1H), 4.76 (m, 1H), 4.90 (q, J=7.0 Hz, 1H), 5.72 (dd, J$_1$=16.1 Hz, J$_2$=5.9 Hz, 1H), 6.62 (d, J=15.7 Hz, 1H), 7.0-7.7 (m, 8H)

IR (KBr disk): 3,050 to 2,850 (w, C—H stretching), 1,720 (s, C=O stretching), 1,550 (m), 1,505 (m, substituted aromatics), 1,345 (m), 1,220 (s), 1,155 (m), 1,100 (w), 970 (w), 835 (m, p substituted aromatics), 740 (m, substituted aromatics)

Example 1

(1) Synthesis of cellulose tris(4-isopropylphenylcarbamate)

50 g of cellulose was dispersed in dry pyridine and 310 g of 4-isopropylphenyl isocyanate (2.0 equivalents to the hydroxyl group in the cellulose) was added to the resultant and the mixture was heated under reflux for 24 hours. The reactant was poured in methanol, and the formed white solid was filtered and dried under reduced pressure to obtain cellulose tris(4-isopropylphenylcarbamate). The results of elemental analysis of carbon, hydrogen, and nitrogen elements of the resultant product are shown in Table 1.

(2) Preparation of packing material for separating optical isomers

The cellulose tris(4-isopropylphenylcarbamate) obtained in the above item (1) was dissolved in acetone and the obtained acetone solution was evenly sprinkled on silica gel having a particle size of 20 μm and then the solvent was evaporated to obtain a packing material having carried cellulose tris(4-isopropylphenylcarbamate).

(3) Preparation of column for separating optical isomers

The packing material prepared in the above item (2) was packed into a stainless steel column having a length of 25 cm and an inner diameter of 0.46 cm by a slurry packing method to prepare a column for separating optical isomers.

Figure 3:
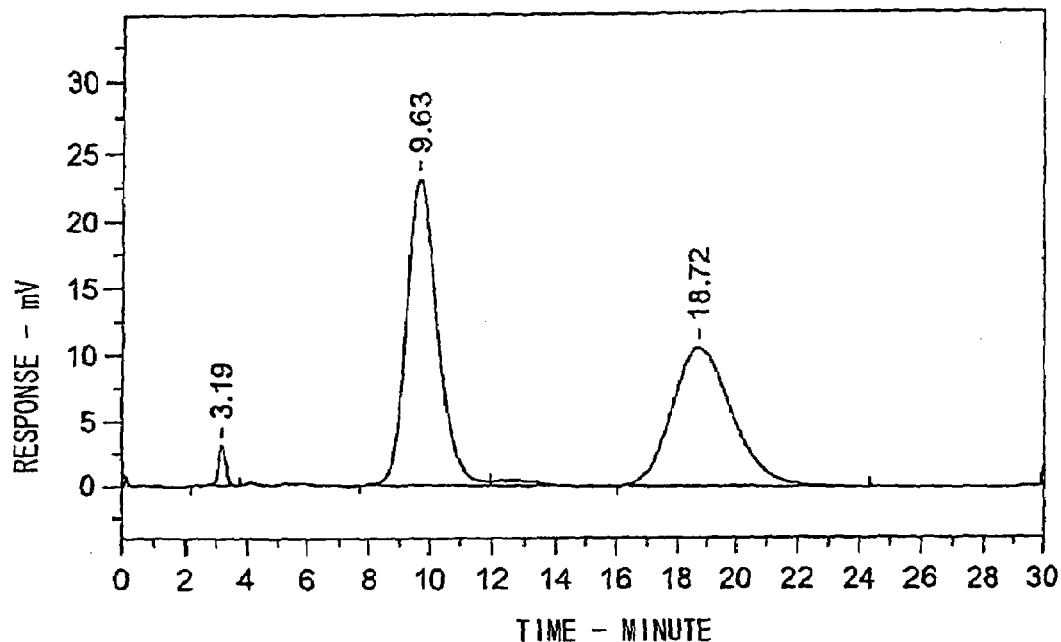
FIG. 3 is a chromatogram of methyl [R*,S*-(E)]-(±)-[3-(4-fluorophenyl)-1-(1-methylethyl)-1H-indol-2-yl]-3,5-dihydroxy-6-heptenoate separated by using a column in Example 1.

(4) Separation of optical isomers of methyl [R*,S*-(E)]-(±)-[3-(4-fluorophenyl)-1-(1-methylethyl)-1H-indol-2-yl]-3,5-dihydroxy-6-heptenoate Using the column for separating optical isomers obtained in the above item (3), methyl [R*,S*-(E)]-(±)-[3-(4-fluorophenyl)-1-(1-methylethyl)-1H-indol-2-yl]-3,5-dihydroxy-6-heptenoate was subjected to optical resolution by liquid chromatography. Table 2 shows the retention coefficient and separation factor in the optical resolution and FIG. 3 shows the chromatogram.

Note that the liquid chromatography was performed using UV-970 manufactured by JASCO Corporation as a measuring apparatus under the following analysis conditions. By measuring the optical rotatory power of the obtained peak component by using an optical rotation detector Advanced Laser Polarimeter manufactured by PDR-Chiral Corporation, it can be confirmed that the detected peak corresponds to an optical isomer. Further, the retention coefficient (k') was calculated from the following equations (1) and (2) and the separation factor (α) was calculated from the following equation (3).

<Analysis Conditions>
Moving phase: Hexane/2-propanol=80/20 (v/v)
Flow rate: 1.0 ml/min
Column temperature 25° C.
Detection wavelength 254 nm $$k_1' = (v_1 - v_0)/v_0$$

(wherein v$_1$ indicates a retention volume (retention time) of a solute component that eluted earlier between each optical isomer and v$_0$ indicates a dead volume (dead time) that is an elution amount (elution time) of tri-tert-butylbenzene.)

$$k_2' = (v_2 - v_0)/v_0$$

(wherein v$_2$ indicates a retention volume (retention time) of a solute component that eluted later between each optical isomer and v$_0$ indicates a dead volume (dead time) that is an elution amount (elution time) of tri-tert-butylbenzene.)

$$\alpha = k_2'/k_1'$$

(wherein v$_1$ or v$_2$ each indicate a retention volume (retention time) of a solute component of each optical isomer and v$_0$ indicates a dead volume (dead time) that is an elution amount (elution time) of tri-tert-butylbenzene.)

Example 2

(1) Synthesis of cellulose tris(4-n-butylphenyl carbamate)

Cellulose tris(4-n-butylphenyl carbamate) was obtained by the same technique as that in Example 1 (1) except that 4-n-butylphenyl isocyanate was used instead of 4-ispropylphenyl isocyanate. The results of elemental analysis of carbon, hydrogen, and nitrogen elements of the resultant product are shown in Table 1.

(2) Preparation of packing material for separating optical isomers

A packing material for separating optical isomers was prepared by the same technique as that in Example 1 (2) except that cellulose tris (4-n-butylphenyl carbamate) obtained in the above item (1) was used.

(3) Preparation of column for separating optical isomers

A column for separating optical isomers was obtained by the same technique as that in Example 1 (3) except that the packing material for separating optical isomers obtained in the above item (2) was used.

Figure 4:
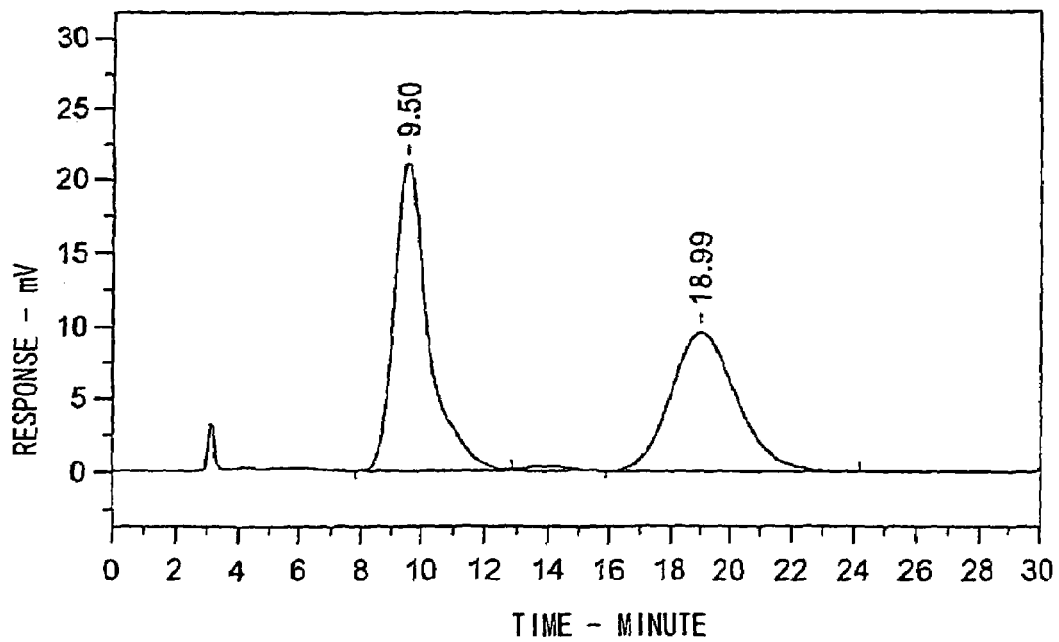
FIG. 4 is a chromatogram of methyl [R*,S*-(E)]-(±)-[3-(4-fluorophenyl)-1-(1-methylethyl)-1H-indol-2-yl]-3,5-dihydroxy-6-heptenoate separated by using a column in Example 2.

(4) Separation of optical isomers of methyl [R*,S*-(E)]-(±)-[3-(4-fluorophenyl)-1-(1-methylethyl)-1H-indol-2-yl]-3,5-dihydroxy-6-heptenoate Using the column for separating optical isomers obtained in the above item (3), methyl [R*,S*-(E)]-(±)-[3-(4-fluorophenyl)-1-(1-methylethyl)-1H-indol-2-yl]-3,5-dihydroxy-6-heptenoate was subjected to optical resolution by liquid chromatography in the same manner as in Example 1. Table 2 shows the retention coefficient and separation factor in the optical resolution and FIG. 4 shows the chromatogram.

Example 3

(1) Synthesis of cellulose tris(4-ethylphenylcarbamate)

Cellulose tris(4-ethylphenyl carbamate) was obtained by the same technique as that in Example 1 (1) except that 4-ethylphenyl isocyanate was used instead of 4-ispropylphenyl isocyanate. The results of elemental analysis of carbon, hydrogen, and nitrogen elements of resultant product are shown in Table 1.

(2) Preparation of packing material for separating optical isomers

A packing material for separating optical isomers was prepared by the same technique as that in Example 1 (2) except that cellulose tris(4-ethylphenyl carbamate) obtained in the above item (1) was used.

(3) Preparation of column for separating optical isomers

A column for separating optical isomers was obtained by the same technique as that in Example 1 (3) except that the packing material for separating optical isomers obtained in the above item (2) was used.

Figure 5:
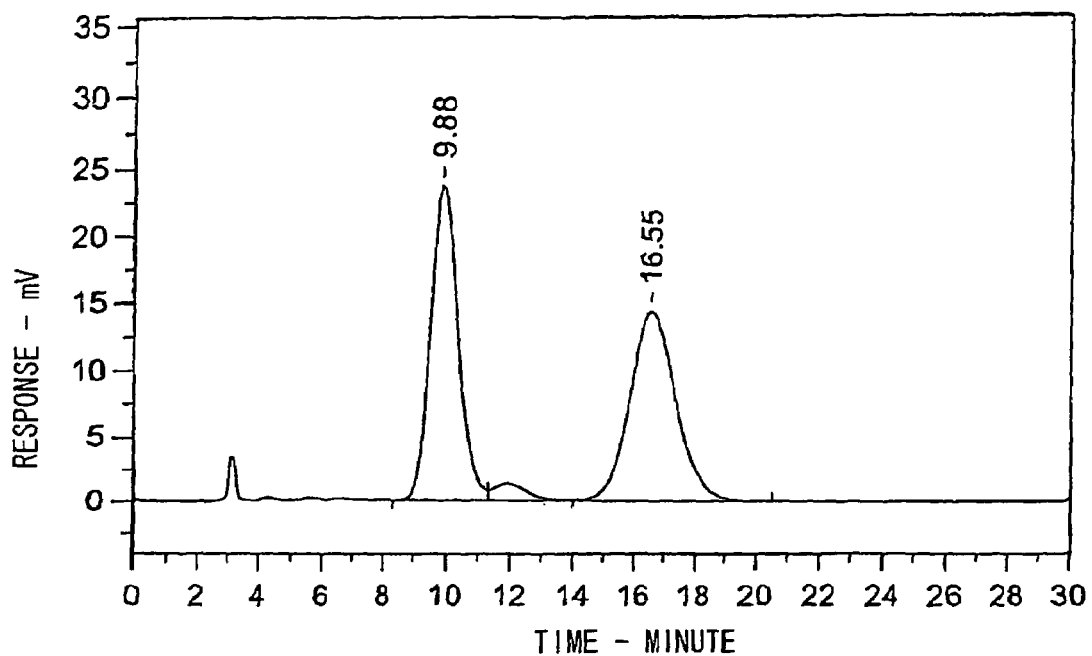
FIG. 5 is a chromatogram of methyl [R*,S*-(E)]-(±)-[3-(4-fluorophenyl)-1-(1-methylethyl)-1H-indol-2-yl]-3,5-dihydroxy-6-heptenoate separated by using a column in Example 3.

(4) Separation of optical isomers of methyl [R*,S*-(E)]-(±)-[3-(4-fluorophenyl)-1-(1-methylethyl)-1H-indol-2-yl]-3,5-dihydroxy-6-heptenoate Using the column for separating optical isomers obtained in the above item (3), methyl [R*,S*-(E)]-(±)-[3-(4-fluorophenyl)-1-(1-methylethyl)-1H-indol-2-yl]-3,5-dihydroxy-6-heptenoate was subjected to optical resolution by liquid chromatography in the same manner as in Example 1. Table 2 shows the retention coefficient and separation factor in the optical resolution and FIG. 5 shows the chromatogram.

Example 4

(1) Synthesis of cellulose tris(4-sec-butylphenyl carbamate)

Cellulose tris(4-sec-butylphenyl carbamate) was obtained by the same technique as that in Example 1 (1) except that 4-sec-butylphenyl isocyanate was used instead of 4-ispropylphenyl isocyanate. The results of elemental analysis of carbon, hydrogen, and nitrogen elements of resultant product are shown in Table 1.

(2) Preparation of packing material for separating optical isomers

A packing material for separating optical isomers was prepared by the same technique as that in Example 1 (2) except that cellulose tris(4-sec-butylphenyl carbamate) obtained in the above item (1) was used.

(3) Preparation of column for separating optical isomers

A column for separating optical isomers was obtained by the same technique as that in Example 1 (3) except that the packing material for separating optical isomers obtained in the above item (2) was used.

Figure 6:
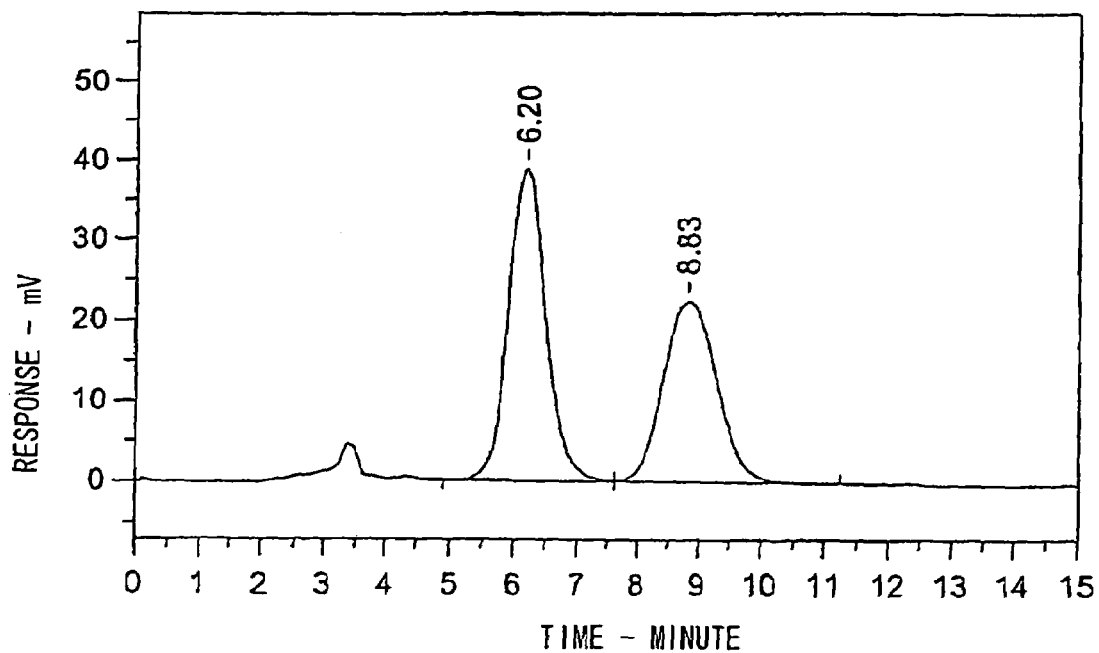
FIG. 6 is a chromatogram of methyl [R*,S*-(E)]-(±)-[3-(4-fluorophenyl)-1-(1-methylethyl)-1H-indol-2-yl]-3,5-dihydroxy-6-heptenoate separated by using a column in Example 4.

(4) Separation of optical isomers of methyl [R*,S*-(E)]-(±)-[3-(4-fluorophenyl)-1-(1-methylethyl)-1H-indol-2-yl]-3,5-dihydroxy-6-heptenoate Using the column for separating optical isomers obtained in the above item (3), methyl [R*,S*-(E)]-(±)-[3-(4-fluorophenyl)-1-(1-methylethyl)-1H-indol-2-yl]-3,5-dihydroxy-6-heptenoate was subjected to optical resolution by liquid chromatography in the same manner as in Example 1. Table 2 shows the retention coefficient and separation factor in the optical resolution and FIG. 6 shows the chromatogram.

Example 5

(1) Synthesis of cellulose tris(4-iso-butylphenyl carbamate)

Cellulose tris(4-iso-butylphenyl carbamate) was obtained by the same technique as that in Example 1 (1) except that 4-iso-butylphenyl isocyanate was used instead of 4-ispropylphenyl isocyanate. The results of elemental analysis of carbon, hydrogen, and nitrogen elements of resultant product are shown in Table 1.

(2) Preparation of packing material for separating optical isomers

A packing material for separating optical isomers was prepared by the same technique as that in Example 1 (2) except that cellulose tris(4-iso-butylphenyl carbamate) obtained in the above item (1) was used.

(3) Preparation of column for separating optical isomers

A column for separating optical isomers was obtained by the same technique as that in Example 1 (3) except that the packing material for separating optical isomers obtained in the above item (2) was used.

Figure 7:
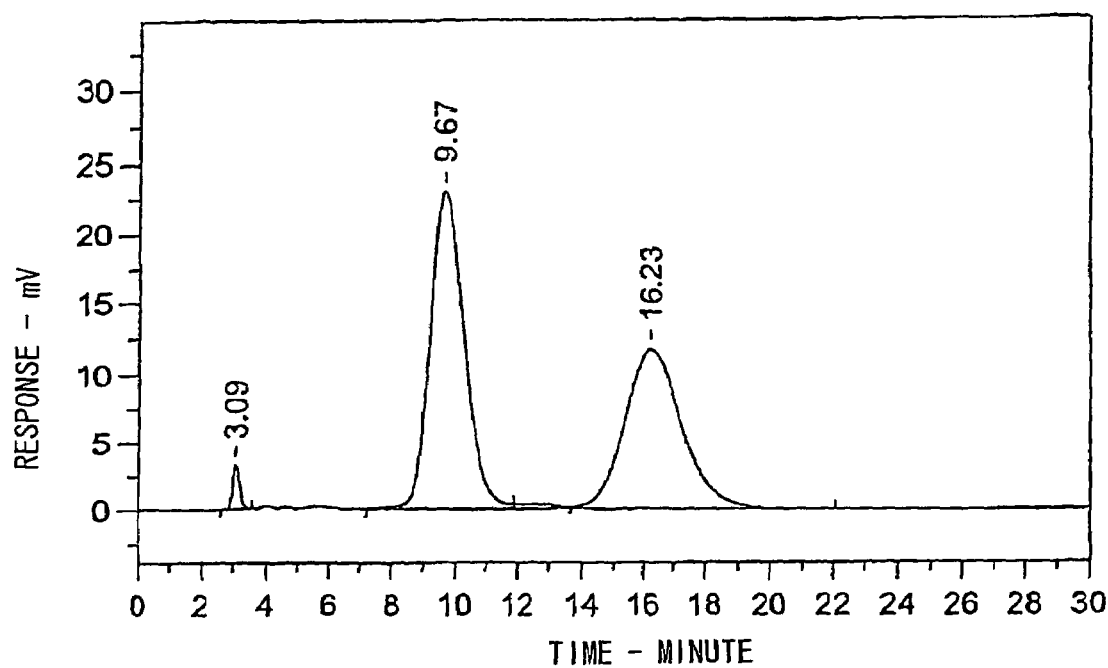
FIG. 7 is a chromatogram of methyl [R*,S*-(E)]-(±)-[3-(4-fluorophenyl)-1-(1-methylethyl)-1H-indol-2-yl]-3,5-dihydroxy-6-heptenoate separated by using a column in Example 5.

(4) Separation of optical isomers of methyl [R*,S*-(E)]-(±)-[3-(4-fluorophenyl)-1-(1-methylethyl)-1H-indol-2-yl]-3,5-dihydroxy-6-heptenoate Using the column for separating optical isomers obtained in the above item (3), methyl [R*,S*-(E)]-(±)-[3-(4-fluorophenyl)-1-(1-methylethyl)-1H-indol-2-yl]-3,5-dihydroxy-6-heptenoate was subjected to optical resolution by liquid chromatography in the same manner as in Example 1. Table 2 shows the retention coefficient and separation factor in the optical resolution and FIG. 7 shows the chromatogram.

TABLE 1

| | Elemental analysis of synthesized polymer | | |
|---|---|---|---|
| | C (%) | H (%) | N (%) |
| Example 1 | 65.67(66.96) | 6.62(6.71) | 6.31(6.51) |
| Example 2 | 67.47(68.10) | 7.04(7.18) | 5.97(6.11) |
| Example 3 | 64.78(65.66) | 6.14(6.18) | 6.96(6.96) |
| Example 4 | 67.86(68.10) | 7.14(7.18) | 6.03(6.11) |
| Example 5 | 67.78(68.10) | 7.09(7.18) | 6.00(6.11) |

Note:
What is described in the brackets ( ) is a theoretical value.

Comparative Example 1

A packing material for separating optical isomers, manufactured by Daicel Chemical Industries, Ltd., CHIRALCEL OG (registered trademark of Daicel Chemical Industries, Ltd., particle size: 20 µm), which is a packing material including silica gel having carried thereon cellulose tris (4-methylphenyl carbamate), was packed into a stainless steel column having a length of 25 cm and an inner diameter of 0.46 cm by a slurry packing method to prepare a column for separating optical isomers.

Figure 8:
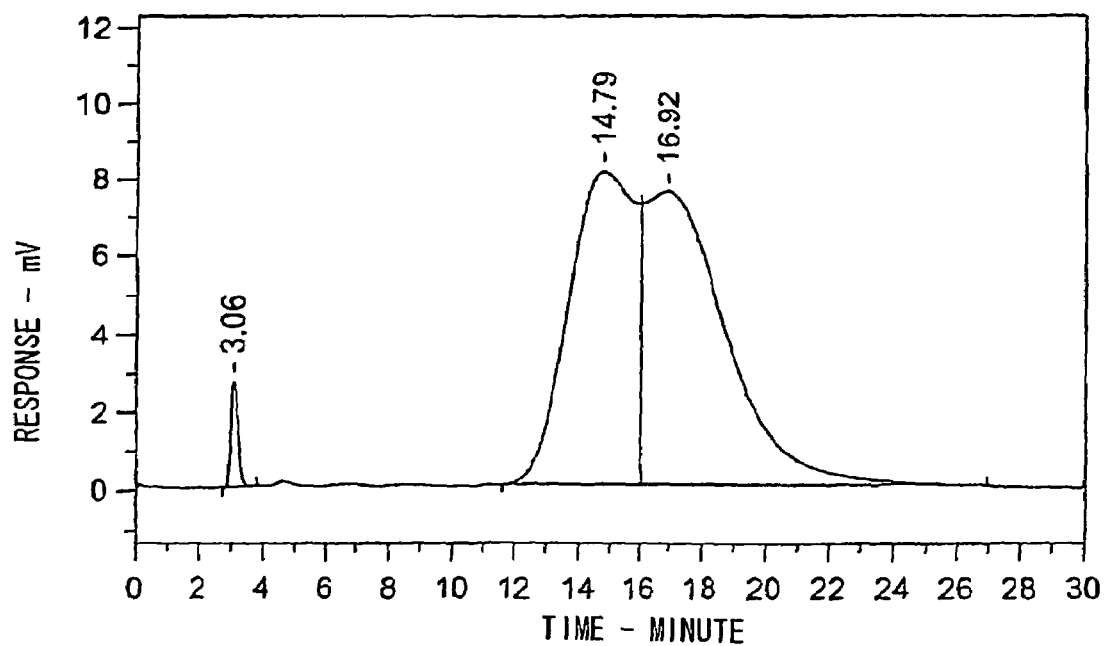
FIG. 8 is a chromatogram of methyl [R*,S*-(E)]-(±)-[3-(4-fluorophenyl)-1-(1-methylethyl)-1H-indol-2-yl]-3,5-dihydroxy-6-heptenoate separated by using a column in Comparative Example 1.

Using the obtained column for separating optical isomers, methyl [R*,S*-(E)]-(±)-[3-(4-fluorophenyl)-1-(1-methylethyl)-1H-indol-2-yl]-3,5-dihydroxy-6-heptenoate was subjected to optical resolution by liquid chromatography in the same manner as in Example 1. Table 2 shows the retention coefficient and separation factor in the optical resolution and FIG. 8 shows the chromatogram.

Comparative Example 2

A packing material for separating optical isomers, manufactured by Daicel Chemical Industries, Ltd., CHIRALCEL OF (registered trademark of Daicel Chemical Industries, Ltd., particle size: 20 µm), which is a packing material including silica gel having carried thereon cellulose tris (4-chlorophenyl carbamate), was packed into a stainless steel column having a length of 25 cm and an inner diameter of 0.46 cm by a slurry packing method to prepare a column for separating optical isomers.

Figure 9:
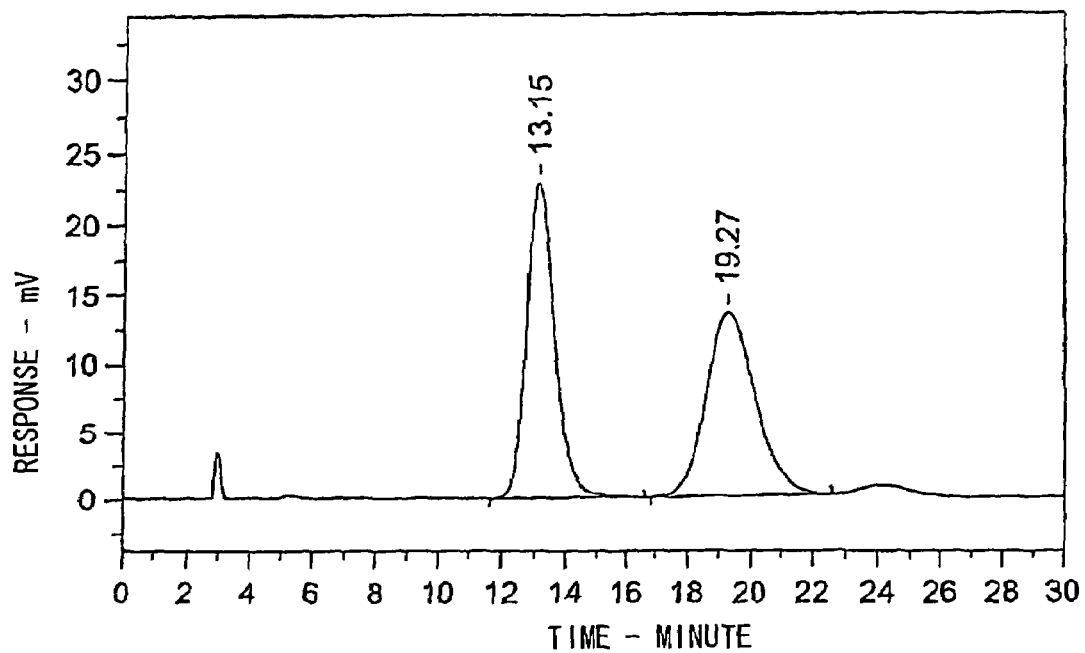
FIG. 9 is a chromatogram of methyl [R*,S*-(E)]-(±)-[3-(4-fluorophenyl)-1-(1-methylethyl)-1H-indol-2-yl]-3,5-dihydroxy-6-heptenoate separated by using a column in Comparative Example 2.
Figure 10:
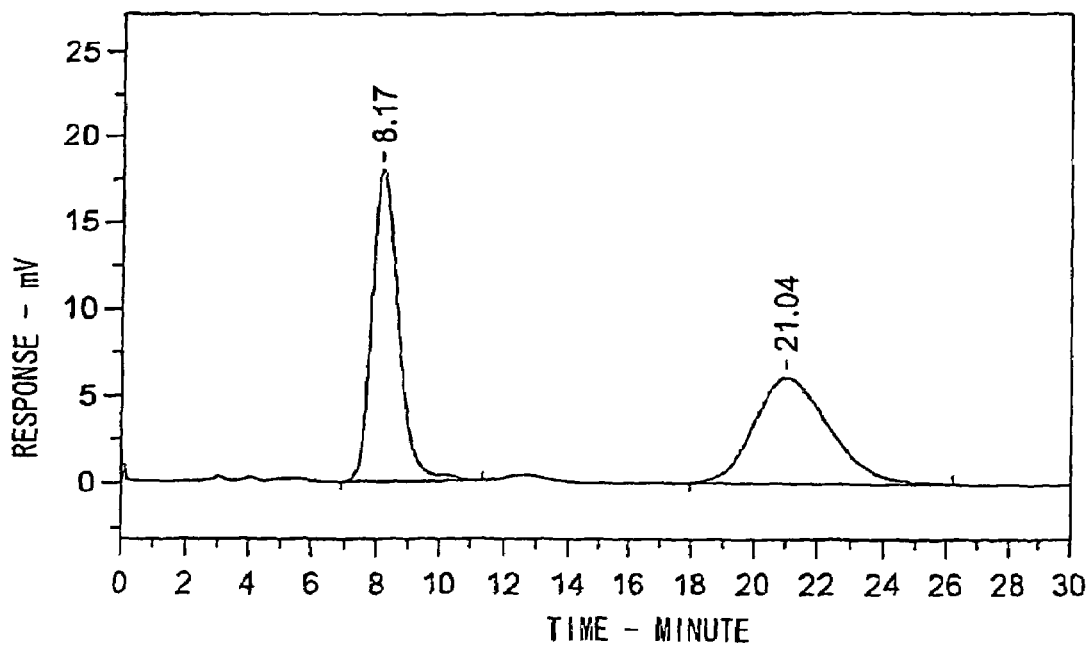
FIG. 10 is a chromatogram of ethyl [R*,S*-(E)]-(±)-[3-(4-fluorophenyl)-1-(1-methylethyl)-1H-indol-2-yl]-3,5-dihydroxy-6-heptenoate separated by using the column in Example 1.
Figure 11:
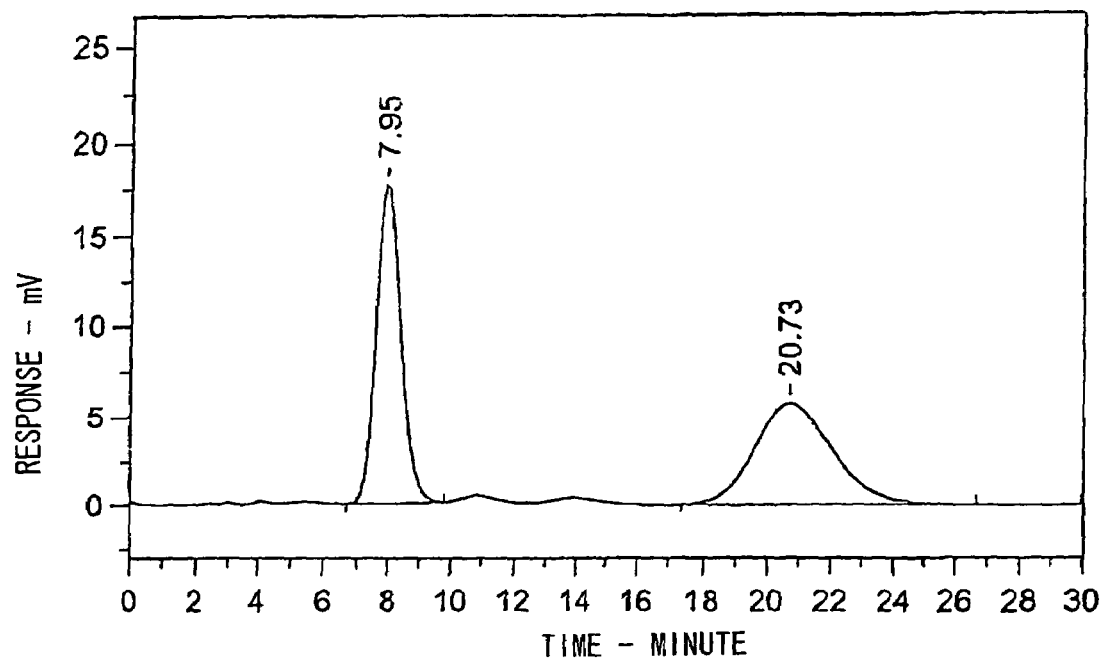
FIG. 11 is a chromatogram of ethyl [R*,S*-(E)]-(±)-[3-(4-fluorophenyl)-1-(1-methylethyl)-1H-indol-2-yl]-3,5-dihydroxy-6-heptenoate separated by using the column in Example 2.
Figure 12:
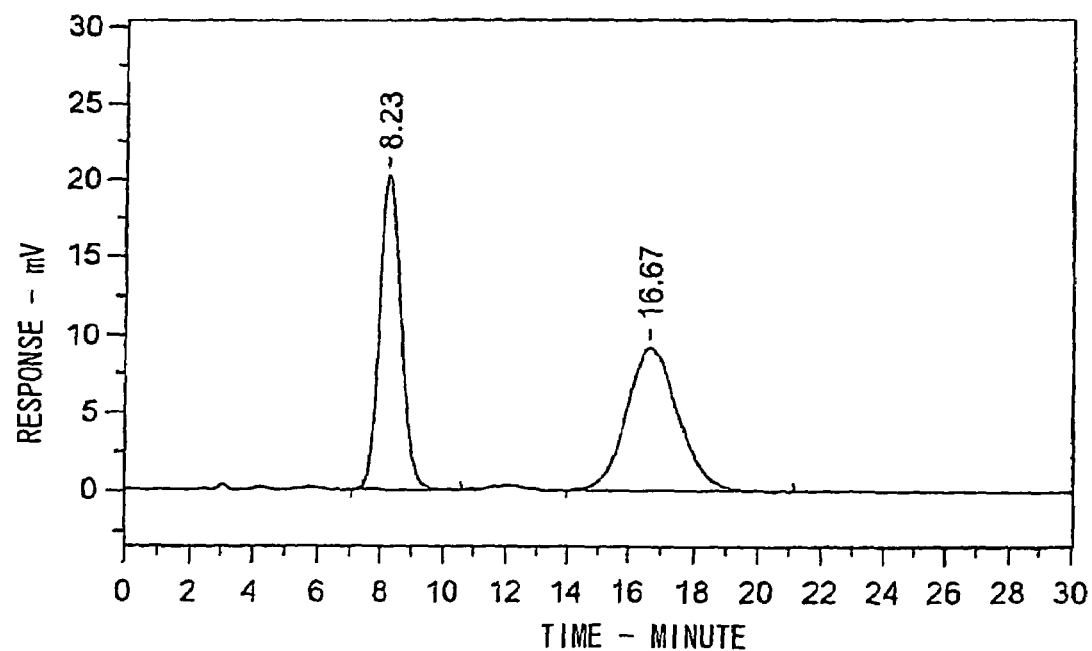
FIG. 12 is a chromatogram of ethyl [R*,S*-(E)]-(±)-[3-(4-fluorophenyl)-1-(1-methylethyl)-1H-indol-2-yl]-3,5-dihydroxy-6-heptenoate separated by using the column in Example 3.
Figure 13:
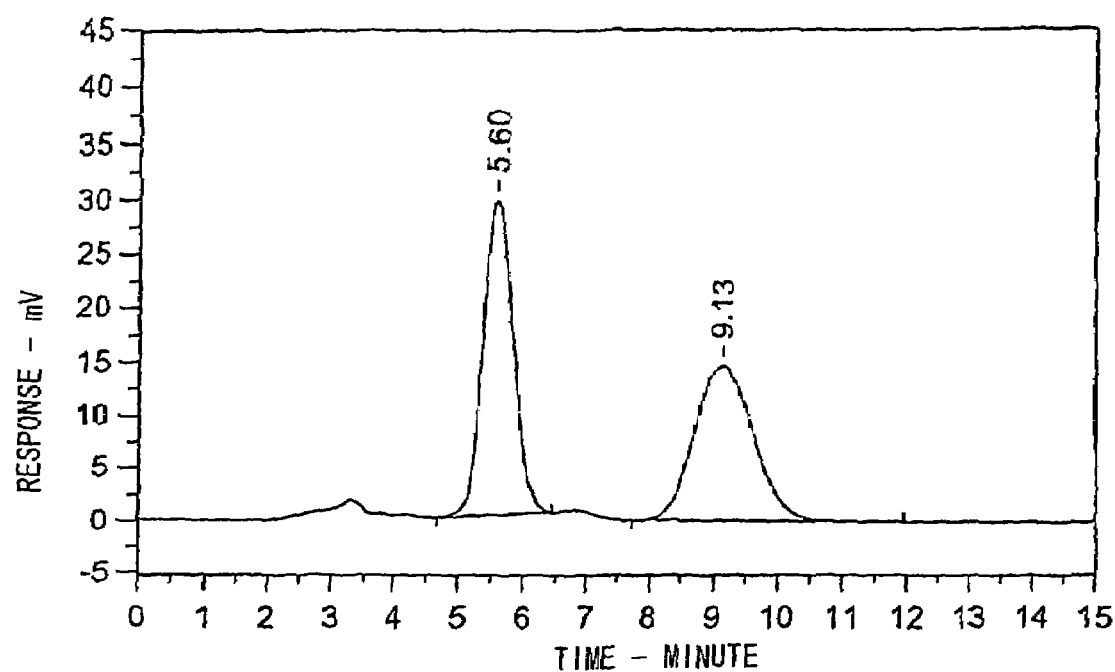
FIG. 13 is a chromatogram of ethyl [R*,S*-(E)]-(±)-[3-(4-fluorophenyl)-1-(1-methylethyl)-1H-indol-2-yl]-3,5-dihydroxy-6-heptenoate separated by using the column in Example 4.
Figure 14:
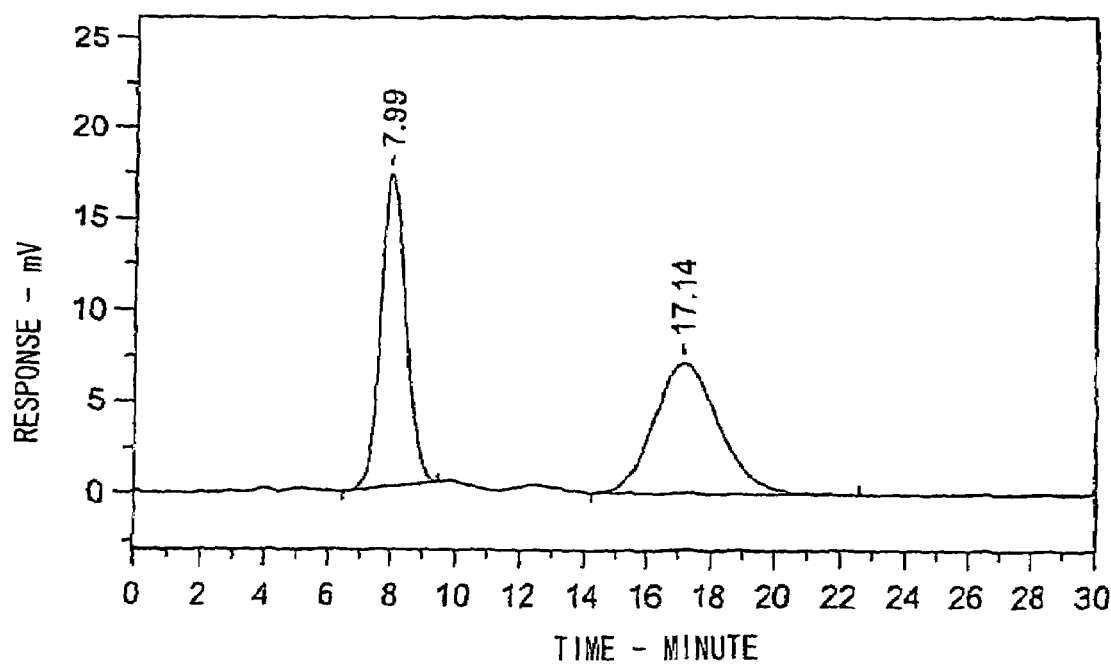
FIG. 14 is a chromatogram of ethyl [R*,S*-(E)]-(±)-[3-(4-fluorophenyl)-1-(1-methylethyl)-1H-indol-2-yl]-3,5-dihydroxy-6-heptenoate separated by using the column in Example 5.

Using the obtained column for separating optical isomers, methyl [R*,S*-(E)]-(±)-[3-(4-fluorophenyl)-1-(1-methylethyl)-1H-indol-2-yl]-3,5-dihydroxy-6-heptenoate was subjected to optical resolution by liquid chromatography in the same manner as in Example 1. Table 2 shows the retention coefficient and separation factor in the optical resolution and FIG. 9 shows the chromatogram.

TABLE 2

Results of optical resolution of methyl [R*,S*-(E)]-(±)-[3-(4-fluorophenyl)-1-(1-methylethyl)-1H-indol-2-yl]-3,5-dihydroxy-6-heptenoate

|  | Example 1 | Example 2 | Example 3 | Example 4 | Example 5 | Comparative Example 1 | Comparative Example 2 |
|---|---|---|---|---|---|---|---|
| Retention coefficient (α) | 2.41 | 2.49 | 1.99 | 1.94 | 2.00 | 1.18 | 1.60 |
| Separation factor (k') | 2.02 | 2.03 | 2.15 | 0.82 | 2.13 | 3.84 | 3.37 |

Examples 6 to 10

Separation of optical isomers of ethyl [R*,S*-(E)]-(±)-[3-(4-fluorophenyl)-1-(1-methylethyl)-1H-indol-2-yl]-3,5-dihydroxy-6-heptenoate prepared in Synthesis Example 2 in stead of methyl [R*,S*-(E)]-(±)-[3-(4-fluorophenyl)-1-(1-methylethyl)-1H-indol-2-yl]-3,5-dihydroxy-6-heptenoate prepared in Synthesis Example 1 was performed in the same manner as in each of Examples 1 to 5. Table 3 shows the retention coefficients and separation factors in the optical resolutions and FIGS. 10 to 14 show the chromatograms, respectively.

Comparative Examples 3 and 4

Figure 15:
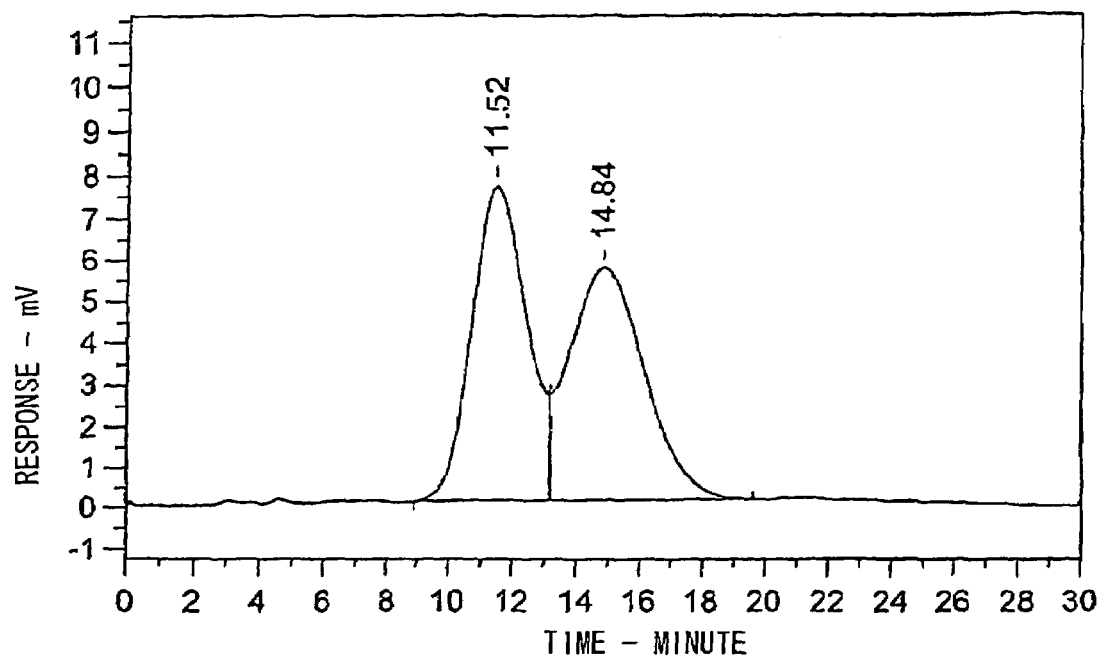
FIG. 15 is a chromatogram of ethyl [R*,S*-(E)]-(±)-[3-(4-fluorophenyl)-1-(1-methylethyl)-1H-indol-2-yl]-3,5-dihydroxy-6-heptenoate separated by using the column in Comparative Example 1.
Figure 16:
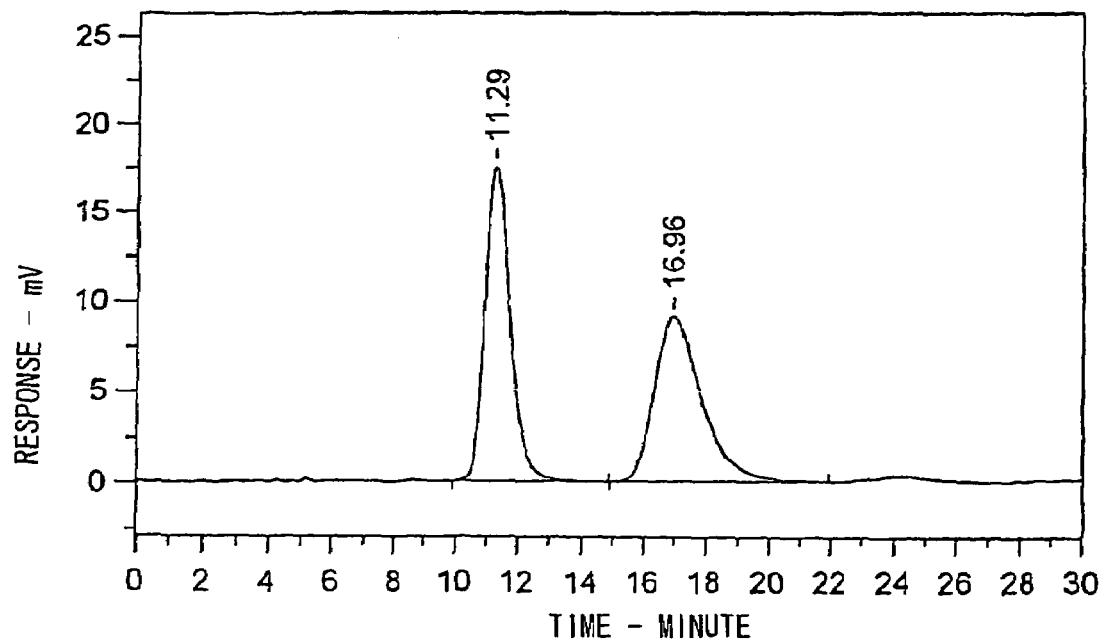
FIG. 16 is a chromatogram of ethyl [R*,S*-(E)]-(±)-[3-(4-fluorophenyl)-1-(1-methylethyl)-1H-indol-2-yl]-3,5-dihydroxy-6-heptenoate separated by using the column in Comparative Example 2.

Separation of optical isomers of ethyl [R*,S*-(E)]-(±)-[3-(4-fluorophenyl)-1-(1-methylethyl)-1H-indol-2-yl]-3,5-dihydroxy-6-heptenoate prepared in Synthesis Example 2 in stead of methyl [R*,S*-(E)]-(±)-[3-(4-fluorophenyl)-1-(1-methylethyl)-1H-indol-2-yl]-3,5-dihydroxy-6-heptenoate prepared in Synthesis Example 1 was performed in the same manner as in each of Comparative Examples 1 and 2. Table 3 shows the retention coefficients and separation factors in the optical resolutions and FIGS. 15 and 16 show the chromatograms, respectively.

Example 11

The packing material for separating optical isomers obtained in Example 1 (2) was packed in eight columns of stainless steel each having an inner diameter of 1.0 cm and a length of 10 cm by a slurry packing method, and the columns were attached to a small simulated moving bed apparatus and fractionation of methyl [R*,S*-(E)]-(±)-[3-(4-fluorophenyl)-1-(1-methylethyl)-1H-indol-2-yl]-3,5-dihydroxy-6-heptenoate synthesized in Synthesis Example 1 was performed. Table 4 shows operation conditions of the small simulated moving bed apparatus and productivity of the raffinate component obtained.

The conditions of fractionation of methyl [R*,S*-(E)]-(±)-[3-(4-fluorophenyl)-1-(1-methylethyl)-1H-indol-2-yl]-3,5-dihydroxy-6-heptenoate by the above-mentioned small simulated moving bed apparatus are shown in the following.

<Conditions of Fractionation>
Moving phase: Hexane/2-propanol=80/20 (v/v)
Column temperature: 40° C.
Detection wavelength: 254 nm
Concentration of mixed solution: 5 g/l (the solvent was the same as the moving phase)<

Examples 12 to 15

Fractionation of methyl [R*,S*-(E)]-(±)-[3-(4-fluorophenyl)-1-(1-methylethyl)-1H-indol-2-yl]-3,5-dihydroxy-6-heptenoate was performed using the small simulated moving bed apparatus in the same manner as in Example 11 except that each of the packing materials for separating optical isomers obtained in Examples 2 (2) to Example 5 (2) was used. Table 4 shows operation conditions of the small simulated moving bed apparatus and productivities of the raffinate component obtained.

TABLE 3

Results of optical resolution of ethyl [R*,S*-(E)]-(±)-[3-(4-fluorophenyl)-1-(1-methylethyl)-1H-indol-2-yl]-3,5-dihydroxy-6-heptenoate

|  | Example 6 | Example 7 | Example 8 | Example 9 | Example 10 | Comparative Example 3 | Comparative Example 4 |
|---|---|---|---|---|---|---|---|
| Retention coefficient (α) | 3.58 | 3.65 | 2.66 | 2.61 | 2.87 | 1.39 | 1.68 |
| Separation factor (k') | 1.56 | 1.54 | 1.63 | 0.65 | 1.59 | 2.77 | 2.76 |

Comparative Example 5

Fractionation of optical isomers of methyl [R*,S*-(E)]-(±)-[3-(4-fluorophenyl)-1-(1-methylethyl)-1H-indol-2-yl]-3,5-dihydroxy-6-heptenoate by the small simulated moving bed apparatus was performed in the same manner as in Example 11 except that the packing material for separating optical isomers provided in Comparative Example 2 was used. Table 4 shows operation conditions of the small simulated moving bed apparatus and productivity of the raffinate component obtained.

Note that the packing material for separating optical isomers provided in Comparative Example 1 showed insufficient separation in the above-mentioned liquid chromatography with a single column and hence the packing material for separating optical isomers was not applied to the above-mentioned small simulated moving bed apparatus.

obtained in Examples 2 (2) to Example 5 (2) was filled in the same manner as in each of Examples 12 to 15, preparatory separation of ethyl [R*,S*-(E)]-(±)-[3-(4-fluorophenyl)-1-(1-methylethyl)-1H-indol-2-yl]-3,5-dihydroxy-6-heptenoate was performed. Table 5 shows operation conditions of the small simulated moving bed apparatus and productivities of the raffinate component obtained.

TABLE 4

|  | Example 11 | Example 12 | Example 13 | Example 14 | Example 15 | Comparative Example 5 |
|---|---|---|---|---|---|---|
| Productivity* (kg-Rac./kg-CSP/day) | 1.20 | 1.38 | 0.81 | 0.93 | 0.84 | 0.70 |
| Flow rate for supplying optical isomer mixed solution (ml/min.) | 7.0 | 6.5 | 4.3 | 10.3 | 9.2 | 3.6 |
| Flow rate of raffinate (ml/min.) | 21.8 | 20.9 | 15.3 | 9.0 | 10.2 | 11.2 |
| Flow rate of extract (ml/min.) | 46.1 | 38.7 | 32.4 | 13.2 | 23.5 | 25.7 |
| Supply flow rate of eluent (ml/min.) | 61.6 | 52.4 | 43.4 | 11.9 | 24.4 | 33.3 |
| Step time (min.) | 14.52 | 15.35 | 14.15 | 5.72 | 9.79 | 13.50 |

*Mass of racemic body that can be treated a day per kg of packing material for separating optical isomers

Example 16

Using the small simulated moving bed apparatus with which the packing material for separating optical isomers obtained in Example 1 (2) was filled in the same manner as in Example 11, fractionation of ethyl [R*,S*-(E)]-(±)-[3-(4-fluorophenyl)-1-(1-methylethyl)-1H-indol-2-yl]-3,5-dihydroxy-6-heptenoate was performed. Table 5 shows operation conditions of the small simulated moving bed apparatus and productivity of the raffinate component obtained.

Examples 17 to 20

Using small simulated moving bed apparatus with which each of the packing materials for separating optical isomers

Comparative Example 6

Fractionation of ethyl [R*,S*-(E)]-(±)-[3-(4-fluorophenyl)-1-(1-methylethyl)-1H-indol-2-yl]-3,5-dihydroxy-6-heptenoate using the small simulated moving bed apparatus with which the packing material for separating optical isomers provided in Comparative Example 2 was filled in the same manner as in Example 16. Table 5 shows operation conditions of the small simulated moving bed apparatus and productivity of the raffinate component obtained.

Note that the packing material for separating optical isomers provided in Comparative Example 1 showed insufficient separation in the above-mentioned liquid chromatography with a single column and hence the packing material for separating optical isomers was not applied to the above-mentioned small simulated moving bed apparatus.

TABLE 5

|  | Example 16 | Example 17 | Example 18 | Example 19 | Example 20 | Comparative Example 6 |
|---|---|---|---|---|---|---|
| Productivity* (kg-Rac./kg-CSP/day) | 1.33 | 1.25 | 0.97 | 1.02 | 1.04 | 0.69 |
| Flow rate for supplying optical isomer mixed solution (ml/min.) | 6.3 | 7.2 | 5.1 | 11.2 | 11.5 | 3.6 |
| Flow rate of raffinate (ml/min.) | 21.8 | 20.9 | 15.9 | 11.1 | 16.0 | 12.6 |
| Flow rate of extract (ml/min.) | 46.1 | 38.7 | 28.7 | 13.2 | 29.0 | 23.0 |
| Supply flow rate of eluent (ml/min.) | 61.6 | 52.4 | 39.6 | 13.1 | 33.5 | 32.0 |
| Step time (min.) | 14.71 | 14.71 | 12.8 | 6.46 | 13.03 | 15.80 |

*Mass of racemic body that can be treated a day per kg of packing material for separating optical isomers

INDUSTRIAL APPLICABILITY

According to the present invention, optically active dihydroxyheptenoic esters can be separated more clearly and can be produced with higher productivity of fractionation.

What is claimed is:

1. A method of separating optically active dihydroxyheptenoic acid esters from a solution comprising a mixture of optical isomers of a dihydroxyheptenoic acid ester represented by the formula (1) below

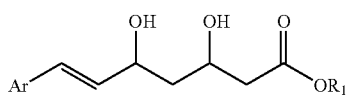
(1)

wherein Ar represents an aromatic group that may have nitrogen, oxygen, and a condensed ring, and have a group selected from a hetero-group having nitrogen and/or oxygen, a halogen group, and a hydrocarbon group which is an alkyl group or phenyl group and may have the hetero-group and the halogen group, $R_1$ represents a linear or branched chain alkyl group having 1 to 20 carbon atoms, a phenyl group, or an aralkyl group having 7 to 18 carbon atoms by liquid chromatography in which a packing material comprising a carrier and a first polysaccharide carried on the carrier is used, wherein the first polysaccharide is formed by substituting for a portion or all of hydrogen atoms in hydroxyl groups and amino groups of a second polysaccharide by one of the groups represented by the formula (2) below and the formula (3) below:

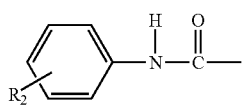
(2)

wherein $R_2$ represents a linear or branched chain alkyl group having 2 to 8 carbon atoms

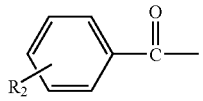
(3)

wherein $R_2$ represents a linear or branched chain alkyl group having 2 to 8 carbon atoms.

2. The method according to claim 1, wherein the second polysaccharide is cellulose or amylose.

3. The method according to claim 1, wherein $R_2$ is connected to a carbon atom at a 4-position of a phenyl group in the formula (2) or the formula (3).

4. The method according to claim 3, wherein $R_2$ is an ethyl group, an isopropyl group, an n-butyl group, an isobutyl group or a sec-butyl group.

5. The method according to claim 2, wherein $R_2$ is connected to a carbon atom at a 4-position of a phenyl group in the formula (2) or the formula (3).

6. The method according to claim 5, wherein $R_2$ is an ethyl group, an isopropyl group, an n-butyl group, an isobutyl group or a sec-butyl group.

7. The method according to claim 1, wherein the liquid chromatography is a simulated moving bed chromatography.

8. The method according to claim 2, wherein the liquid chromatography is a simulated moving bed chromatography.

9. The method according to claim 3, wherein the liquid chromatography is a simulated moving bed chromatography.

10. The method according to claim 4, wherein the liquid chromatography is a simulated moving bed chromatography.

11. The method according to claim 5, wherein the liquid chromatography is a simulated moving bed chromatography.

12. The method according to claim 6, wherein the liquid chromatography is a simulated moving bed chromatography.

* * * * *